United States Patent
Nedez

(12) 
(10) Patent No.: US 6,288,299 B1
(45) Date of Patent: Sep. 11, 2001

(54) METHOD FOR ELIMINATING INHIBITORS OF POLYMERIZATION OF MONOMER MIXTURES USING AN OPTIMIZED ALUMINA

(75) Inventor: Christophe Nedez, Salindres (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/341,959

(22) PCT Filed: Jan. 13, 1998

(86) PCT No.: PCT/FR98/00051

§ 371 Date: Sep. 10, 1999

§ 102(e) Date: Sep. 10, 1999

(87) PCT Pub. No.: WO98/32715

PCT Pub. Date: Jul. 30, 1998

(30) Foreign Application Priority Data

Jan. 22, 1997 (FR) .................................................. 97/00623

(51) Int. Cl.⁷ ........................................................ C07C 7/12
(52) U.S. Cl. .......................... 585/823; 585/824; 585/825
(58) Field of Search ..................................... 585/823, 824, 585/825

(56) References Cited

U.S. PATENT DOCUMENTS 3,240,830   3/1966  Dye .
4,547,619  10/1985  Diaz .

FOREIGN PATENT DOCUMENTS 1 361 512   4/1963  (FR) .
2 248 627   4/1992  (GB) .

OTHER PUBLICATIONS

H–151 Activated Alumina Gel, Sep. 1981.*
Database WPI, Section CH, Week 8816, Derwent Publications Ltd., London, GB; AN 88–108795, XP002040332 & JP 63 057 538 A (Mitsui Toatsu), Mar. 12, 1988, see abstract.

* cited by examiner

*Primary Examiner*—Walter D. Griffin
*Assistant Examiner*—Tam M. Nguyen
(74) *Attorney, Agent, or Firm*—Burns, Doane, Swecker & Mathis, L.L.P.

(57) ABSTRACT

The invention relates to a process for adsorption of polymerization inhibitors from ethylenically unsaturated monomers, in which these inhibitors are placed in contact with an alumina exhibiting a volume of pores of diameter greater than 100 Å of at least 0.20 ml/g, preferably of at least 0.25 ml/g, still more preferably of at least 0.30 ml/g, and a specific surface of at least 30 m²/g, preferably of at least 60 m²/g, still more preferably of at least 80 m²/g.

17 Claims, No Drawings

METHOD FOR ELIMINATING INHIBITORS OF POLYMERIZATION OF MONOMER MIXTURES USING AN OPTIMIZED ALUMINA

The present invention relates to a new process for removing polymerization inhibitors from monomer mixtures, especially from ethylenically unsaturated monomers.

In the industry of polymerization of a large number of ethylenic monomers an important problem has to do with the storage and/or transport of these monomers. This is because an uncontrolled spontaneous polymerization of these monomers in the course of time, starting from free radicals, can be observed. These ethylenically unstable monomers are especially those which have a second unsaturation such as a COOH, C=O, C≡N, C=C, C=S or C=N functional group; they may be, for example, the following monomers: styrene, butadiene, isoprene, (meth)acrylic esters, acrylonitrile, acrolein, chloroprene, vinyl acetate, etc.

To avoid this degradation of the monomers it is known to stabilize them by means of inhibiting substances which prevent polymerization from taking place.

These substances, more generally known as "polymerization inhibitors" can be chosen from picric acid, nitroaromatics, quinone derivatives (hydroquinone, benzoquinone), naphthols, amines (p-phenylenediamine, phenothiazine), phosphites, p-methoxyphenol, p-tert-butylcatechol, etc.

When is it desired to employ inhibited monomers in order to polymerize them or to use them in chemical reactions, it is often necessary to remove the polymerization inhibitors. A number of means are employed for this purpose:

it is possible to add a large quantity of initiator to the reactor to combat the effect of the inhibitor; however, this technique is not suitable in every case, the temperature can be raised considerably to produce the thermolysis of the inhibitor, but the monomer must have a high thermal stability, the charge of monomers and of inhibitor can be distilled, but the monomer must exhibit good thermal stability; in addition, such an operation is difficult to carry out on an industrial scale, and the boiling point of the inhibitor is in many cases higher than that of the monomer, the inhibitor can be removed by adding a dilute solution, for example of sodium hydroxide, the monomer charge being subsequently washed with water in order to remove all traces of caustic compounds; however, the treatment of the liquid effluents also presents industrial problems, lastly, the inhibitor can be adsorbed with the aid of a compound such as alumina, silica gel, activated carbon, calcium oxide, aluminium silicate, talc, calcium sulphates, magnesium sulphates, copper sulphates, magnesium silicate clays, a resin etc.

Adsorption is one of the most advantageous methods because it does not exhibit any of the abovementioned disadvantages. Among the adsorbents employed, activated alumina is preferred.

The objective of the present invention is to propose a new alumina for the adsorption of polymerization inhibitors from ethylenically unsaturated monomers, exhibiting adsorption capacities which are improved in relation to the aluminas of the prior art.

To this end the invention relates to a process for adsorption of polymerization inhibitors from ethylenically unsaturated monomers, in which these inhibitors are placed in contact with an alumina, the said alumina exhibiting a volume of pores of diameter greater than 100 Å of at least 0.20 ml/g. preferably of at least 0.25 ml/g, still more preferably of at least 0.30 ml/g, and a specific surface of at least 30 m$^2$/g, preferably of at least 60 m$^2$/g, still more preferably of at least 80 m$^2$/g.

The volume of the pores of diameter greater than 100 Å represents the cumulative volume created by all the pores of size greater than a diameter of 100 Å. These volumes are measured by the mercury intrusion technique, in which Kelvin's law is applied.

The specific surface indicated is a surface measured by the BET method. A surface measured by the BET method is intended to mean the specific surface determined by nitrogen adsorption in accordance with ASTM standard D 3663-78 established from the Brunauer—Emmett—Teller method described in the periodical "The Journal of the American Chemical Society", 60, 309 (1938).

The sum total of these two characteristics ensures a high adsorption of the polymerization inhibitors by the alumina when compared with the aluminas employed in the prior art.

The alumina may, for example, be in the form of beads, extrudates or monoliths.

The processes for the preparation of the aluminas exhibiting the pore volume and specific surface characteristics which are necessary for making use of the process according to the invention are known to a person skilled in the art.

Insofar as the specific surface is concerned, this may be controlled especially by the calcination (or activation) temperature of the aluminas following their forming.

In the case of the pore volume, its control is due essentially to the choice of the starting alumina employed for the forming and to the operating conditions of forming of the alumina. A person skilled in the art knows these conditions. Some examples are given below.

If the alumina employed is in the form of beads, these beads may be produced by forming by a rotational technique or by drop (so-called oil-drop) coagulation.

Forming by a rotational technique is an agglomeration of the alumina produced by placing the alumina in contact and rotating it about itself. The rotary coating pan and the rotating drum may be mentioned as equipment used for this purpose.

This type of process makes it possible to obtain beads of controlled pore sizes and distributions, these sizes and these distributions being, in general, created during the agglomeration stage.

The porosity may be created by various means, like the choice of the particle size of the alumina powder or the agglomeration of several alumina powders of different particle sizes. Another method consists in mixing with the alumina powder, before or during the agglomeration stage, a compound known as a pore-former, which disappears completely on heating and thus creates a porosity in the beads.

Pore-forming compounds employed which may be mentioned by way of example are wood flour, charcoal, sulphur, tars, plastics or plastic emulsions such as polyvinyl chloride, polyvinyl alcohols, naphthalene or the like. The quantity of the pore-forming compounds added is determined by the desired pore volume.

The alumina powder employed as starting material can be obtained by conventional processes such as the precipitation or gel process and the process using rapid dehydration of alumina hydroxide such as Bayer hydrate (hydrargillite).

This last alumina is obtained especially by rapid dehydration of hydrargillite with the aid of a stream of hot gases, the entry temperature of the gases into the equipment generally varying approximately from 400 to 1200° C., the contact time of the alumina with the hot gases being generally between a fraction of a second and 4–5 seconds; such a process for preparing alumina powder has been described particularly in patent FR-A-1 108 011. This last alumina is that preferred in the invention.

The control of the volumes of the pores of given diameter can also be carried out during this agglomeration stage by suitable adjustment of the rate of introduction of the alumina powder and optionally of water, of the speed of rotation of the equipment or by the introduction of a forming initiator.

Following this agglomeration, the beads obtained may be subjected to various operations intended to improve their mechanical strength, such as maturing by holding in an atmosphere of controlled moisture content, followed by calcining and then an impregnation of the beads with a solution of one or more acids and a hydrothermal treatment in a confined atmosphere. Finally, the beads are dried and calcined so as to be activated.

Forming by drop coagulation consists in introducing drops of an aqueous solution based on an aluminium compound into a water-immiscible liquid (oil, kerosene, etc) such that the drops form substantially spherical particles; these particles are coagulated simultaneously with and/or subsequently to the spheroidal forming, by a gelling agent. The beads are afterwards recovered and then dried and calcined.

Beads of this type can be prepared, for example, according to the process described in patent EP-A-097 539, by coagulation as drops of a suspension or of an aqueous dispersion of alumina or of a solution of a basic aluminium salt which is in the form of an emulsion consisting of an organic phase, an aqueous phase and a surface agent or an emulsifier. The said organic phase may in particular be a hydrocarbon; the surface-active or emulsifying agent is, for example, Galoryl EM® 10.

These beads can also be prepared according to the process described in patent EP-A-015 801 by mixing, at a pH lower than 7.5, an ultrafine boehmite sol and spheroidal alumina particles, then drop coagulation of this mixture as indicated above and, finally, drying and calcining.

The alumina may also be in the form of alumina extrudates. These are generally obtained by blending and then extruding an alumina-based material, and, lastly, calcining. The starting material may be of very varied nature: it may be produced by a partial and rapid dehydration of hydrargillite, according to the teaching of application FR-A-1,108,011, or by precipitation of boehmite, pseudoboehmite or bayerite alumina or of a mixture of these aluminas. During the blending the alumina may be mixed with additives, especially pore-formers as defined above.

These extrudates may exhibit all kinds of shapes, solid or hollow cylinders, multilobes, etc.

In the process according to the invention use is made essentially of an alumina which is in the form of beads originating from forming by a rotational technique.

In general, aluminas of particle size of between 0.8 and 10 mm, preferably between 1 and 5 mm, are used. In the case of forming by drop coagulation the particle size corresponds to the bead diameter and, in the case of extrudates, to the diameter of their cross-section.

The process according to the invention preferably uses as adsorbent an alumina including at least one compound of an element chosen from the alkali metals, the rare earths and the alkaline-earth metals.

This compound may be an oxide, a hydroxide, a salt or a mixture of these. For example, in addition to hydroxides, the sulphates, nitrates, halides, acetates, formates, carbonates and carboxylic acid salts may be mentioned.

Elements chosen from sodium, potassium, lithium, lanthanum and cerium are preferably employed.

The content of alkali metal, alkaline-earth metal or rare-earth element is generally at least 5 mmol per 100 g of alumina, preferably at most 400 mmol, more preferably still between 10 and 400 mmol.

According to a preferred alternative form the alkali metal element is sodium and its content is between 15 and 300 mmol per 100 of alumina.

The deposition of the compound of the dopant element on or in the alumina can be carried out by any method known to a person skilled in the art. It may be carried out, for example, by impregnation of the alumina already prepared with the alkali metal, rare-earth or alkaline-earth metal elements or precursors of these elements, or by mixing the alkali metal, rare-earth or alkaline-earth metal elements or precursors with alumina in the course of the forming of these materials. These elements may also be introduced into the alumina by coprecipitation of the alumina and of the alkali metal, rare-earth or alkaline-earth metal elements or of their precursors.

The alumina used in the process of the invention is preferably prepared by:
  impregnation of alumina with a solution of a compound of an element or of a mixture of compounds,
  drying of the said impregnated alumina,
  heat treatment of the said alumina.

The impregnation is carried out in a known manner by placing the alumina in contact with a solution, a sol or a gel including at least one alkali metal, rare-earth or alkaline-earth metal element in the form of oxide or salt or of one of their precursors.

The operation is carried out in general by soaking the alumina in a determined volume of solution of at least one precursor of an alkali metal, rare-earth or alkaline-earth metal element. Solution of a precursor of one of these elements is intended to mean a solution of a salt or compound of the element or of at least one of the alkali metal, rare-earth or alkaline-earth metal elements, it being possible for these salts and compounds to be thermally decomposed to oxides.

The salt concentration of the solution is chosen as a function of the quantity of element to be deposited on the alumina.

According to a preferred method these elements are deposited by dry impregnation, that is to say that the impregnation is carried out with just the volume of solution needed for the said impregnation, without excess.

The heat treatment is carried out at a temperature determined as a function either of the temperature of use of the alumina or of the desired specific surface. It may also be possible to carry out a heat treatment to obtain an at least partial thermal degradation of the compound, for example in oxide form. However, this degradation is not necessary and, to give an example, it is not necessary especially when compounds such as chlorides, nitrates or hydroxides are employed.

The heat treatment may, for example, be carried out at a temperature which is between 150 and 1000° C., preferably between 300 and 800° C.

The adsorption process according to the invention is suitable when the polymerization inhibitor is chosen, for example, from picric acid, nitroaromatics, quinone derivatives (hydroquinone, benzoquinone), naphthols, amines (p-phenylenediamine, phenothiazine), phosphites, p-methoxyphenol and p-tert-butylcatechol. Particularly good results are obtained for the adsorption of p-tert-butylcatechol.

When purifying an ethylenically unsaturated monomer stabilized with a polymerization inhibitor is involved, the alumina is placed in contact with the said mixture of ethylenically unsaturated monomer and inhibitor, for example at ambient temperatures.

The monomer charge may be based on any type of ethylenically unsaturated monomer such as especially: styrene, butadiene, isoprene, vinyl chloride, vinylidene chloride, tetrafluoroethylene, trifluorochloroethylene, chloroprene, allyl alcohol, vinyl ether, vinyl ester (vinyl acetate), alkyl acrylates and methacrylates (methacrylate, butyl acrylate, ethyl acrylate, 2-ethylhexyl acrylate, methyl methacrylate, ethyl methacrylate, 2-ethylhexyl methacrylate, etc.), acrolein, acrylonitrile, acrylamide, vinylamine, etc., or mixtures thereof.

In general, the mixture of ethylenically unsaturated monomer and of inhibitor includes 2 to 2000 ppm by weight per volume of inhibitor, preferably 5 to 1500 ppm.

The following examples illustrate the invention without, however, limiting its scope.

EXAMPLES

Example 1

The alumina samples tested are pretreated under a stream of air of nitrogen at 300° C. for 2 hours in order to remove any trace of moisture following their storage and in order to make it possible to compare their effectiveness in identical conditions.

1 g of alumina (solids content) thus pretreated is introduced into 200 ml of a solution of cyclohexane containing 500 ppm (by weight/volume) of p-tert-butylcatechol (TBC). The temperature is maintained at 25° C. The content of TBC present in the solution is analysed, in the course of time, by UV-visible.

The degree of adsorption of TBC is deduced from this.

The characteristics of the aluminas employed are combined in Table 1.

TABLE 1

| Aluminas* | BET surface ($m^2/g$) | V100 Å (ml/g) | Particle size (mm) | % by weight TBC adsorbed after 160 h of reaction |
|---|---|---|---|---|
| 1 (comp.) | 328 | 0.05 | 1.4–2.8 | 47 |
| 2 (comp.) | 349 | 0.095 | 2–5 | 38 |
| 3 (comp.) | 272 | 0.06 | 1.4–2.8 | 52 |
| 4 (comp.) | 8 | 0.52 | 2–4 | 8 |
| 5 | 158 | 0.23 | 1.4–2.8 | 72 |
| 6 | 107 | 0.38 | 1.4–2.8 | 71.5 |
| 7 | 190 | 0.45 | 2.4–4 | 91 |
| 8 | 139 | 1.14 | 1.4–2.8 | 87 |

Example 2

The alumina samples tested are pretreated under a stream of air of nitrogen at 300° C. for 2 hours in order to remove any trace of moisture following their storage and in order to make it possible to compare their effectiveness in identical conditions.

1 g of alumina (solids content) thus pretreated is introduced into 200 ml of a solution of styrene containing 500 ppm (by weight/volume) of p-tert-butylcatechol (TBC). The temperature is maintained at 25° C. After 21 hours the proportion of TBC present in the solution is analysed by UB-visible.

The degree of adsorption of TBC is deduced from this.

The characteristics of the aluminas employed are combined in Table 2.

TABLE 2

| Alumina | BET surface ($m^2/g$) | V100 Å (ml/g) | Particle size (mm) | % by weight TBC adsorbed after 21 h |
|---|---|---|---|---|
| 1 (comp.) | 328 | 0.05 | 1.4–2.8 | 31 |
| 8 | 139 | 1.14 | 1.4–2.8 | 75 |

Example 3

Alumina 6 of Example 1 is treated with a potassium compound.

The impregnation is carried out dry with the aid of a solution of potassium carbonate. The impregnated alumina is then dried overnight at 130° C. and then calcined at 470° C. for 1 h 30 min.

The alumina samples tested are pretreated under a stream of air of nitrogen at 300° C. for 2 hours in order to remove any trace of moisture following their storage and in order to make it possible to compare their effectiveness in identical conditions.

1 g alumina (solids content) thus pretreated is introduced into 200 ml of a solution of cyclohexane containing 500 ppm (by weight/volume) of p-tert-butylcatechol (TBC). The temperature is maintained at 25° C. After 160 hours the content of TBC present in the solution is analysed by UV-visible.

The degree of adsorption of TBC is deduced from this.

The characteristics of the aluminas employed are combined in Table 3.

TABLE 3

| Starting alumina | Nature of the element | Element content (mmol/100 g alumina) | % by weight TBC adsorbed after 160 h |
|---|---|---|---|
| Alumina 6 | K | 66 | 88 |

What is claimed is:

1. Process for absorption of polymerization inhibitors in which these inhibitors are placed in contact with an alumina, wherein the said alumina exhibits a volume of pores of diameter greater than 100 Å of at least 0.20 ml/g, and a specific surface of at least 30 $m^2/g$.

2. Process according to claim 1, wherein the alumina is in the form of beads produced by forming by a rotational technique.

3. Process according to claim 2, wherein the beads have a particle size of between 0.8 and 10 mm.

4. Process according to claim 1, the alumina includes at least one compound of an element comprising the alkali metals, the alkaline-earth metals or the rare earths.

5. Process according to claim 4, wherein the alumina includes at least one compound comprising: sodium, potassium, lithium, lanthanum or cerium.

6. Process according to claim 4, wherein the alumina includes at least 5 mmol of at least one alkali metal, alkaline-earth metal or rare-earth element per 100 g of alumina.

7. Process according to claim 1, wherein the inhibitor is picric acid, a nitroaromatic, a quinone derivative, a naphthol, an amine, a phosphite, p-methoxyphenol or p-tert-butylcatechol.

8. Process according to claim 1, wherein the alumina is placed in contact with a mixture of ethylenically unsaturated monomer and of inhibitor.

9. Process according to the preceding claim 8, wherein the mixture of ethylenically unsaturated monomer and of inhibitor comprises 2 to 2000 ppm by weight per volume of inhibitor.

10. The process according to claim 1, wherein said alumina exhibits a volume of pores having a diameter greater than 100 Å of at least 0.25 ml/g.

11. The process according to claim 10, wherein said alumina exhibits a volume of pores having a diameter greater than 100 Å of at least 0.30 ml/g.

12. The process according to claim 1, wherein said alumina has a specific surface of at least 60 $m^2/g$.

13. The process according to claim 12, wherein said alumina has a specific surface of at least 60 $m^2/g$.

14. The process according to claim 3, wherein the beads have a particle size of between 1 and 5 mm.

15. The process according to claim 7, wherein said quinone derivative is hydroquinone or benzoquinone.

16. The process according to claim 9, wherein the mixture of ethylenically unsaturated monomer and of inhibitor comprises 5 to 1500 ppm by weight per volume of inhibitor.

17. A process comprising:

contacting alumina exhibiting a volume of pores having a diameter greater than 100 Å of at least 0.20 ml/g and a specific surface of a least 30 $m^2/g$ with a mixture of at least one ethylenically unsaturated monomer and an inhibitor; and adsorbing the inhibitor with the alumina.

* * * * *